United States Patent [19]

Houlihan et al.

[11] 3,998,850

[45] Dec. 21, 1976

[54] SUBSTITUTED-4'-AMINOACETYL ALKANOYLPHENONES

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Jan. 8, 1975

[21] Appl. No.: 539,352

Related U.S. Application Data

[62] Division of Ser. No. 403,009, Oct. 3, 1973, Pat. No. 3,873,539.

[52] U.S. Cl. .............................................. 260/340.9
[51] Int. Cl.$^2$ ....................................... C07D 317/10
[58] Field of Search ................................. 260/340.9

[56] References Cited

OTHER PUBLICATIONS

C.A. 70:114911y.

*Primary Examiner*—Ethel G. Love
*Attorney, Agent, or Firm*—Gerald D. Sharkin; Robert S. Honor

[57] ABSTRACT

Substituted -4'-aminoacetyl alkanoylphenones, e.g., 4'-(4-methyl-1-piperazinylacetyl)pivalophenone, are prepared by treating corresponding 4'-(haloacetyl)alkanoylphenones with substituted amines, and are useful as hypolipidemic agents.

1 Claim, No Drawings

SUBSTITUTED-4'-AMINOACETYL ALKANOYLPHENONES

This is a division of application Ser. No. 403,009, filed Oct. 3, 1973, now U.S. Pat. No. 3,873,539.

This invention relates to substituted-4'-aminoacetyl alkanoylphenones which exhibit hypolipidemic activity. In particular, it relates to substituted 4'-aminoacetyl pivalophenones, their preparation, pharmaceutically acceptable acid addition salts and intermediates thereof.

The compounds of this invention may be represented by the following structural formula:

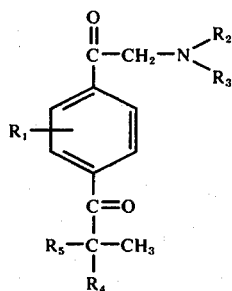

where
$R_1$ represents hydrogen, halo having an atomic weight of about 19 to 36, or straight chain lower alkoxy, i.e., lower alkoxy having 1 to 4 carbon atoms, e.g., methoxy, ethoxy or the like, and
$R_2$ and $R_3$ each independently represent lower alkyl having 1 to 2 carbon atoms, i.e. methyl or ethyl, or
$R_2$ and $R_3$ together with N represent

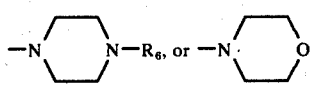

where
$R_6$ represents lower alkyl as defined above, and $R_4$ and $R_5$ each independently represent lower alkyl as defined above.

The compounds of formula (I) are prepared according to the following reaction scheme:

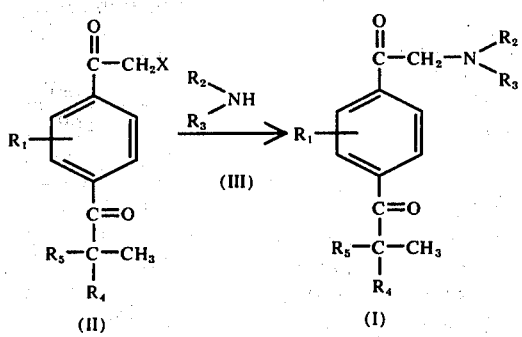

where
X is halo having an atomic weight of 35 to 80
$R_1$, $R_2$, $R_3$, $R_4$ and $R_5$ are as set out above.

The compounds of formula (I) are prepared by treating a compound of the formula (II) with a substituted amine of the formula (III) in the presence of an organic solvent. Although the particular solvent employed is not critical, the preferred solvents include the ethers such as ethyl ether or diethyl ether, the halogenated hydrocarbons such as chloroform, carbon tetrachloride and the like, aromatic hydrocarbons such as benzene, toluene and the like or an excess of a compound of formula (III), especially benzene. The temperature of the reaction is not critical, but it is preferred that the reaction be carried out at a temperature of about 0° C to the reflux temperature of the solvent, especially from about 25° to 30° C. The reaction may be run from about 2 to 24 hours, preferably from about 16 to 20 hours. The compounds of formula (I) are recovered by conventional techniques, e.g., recrystallization.

The compounds of formula (II) are prepared according to the following reaction scheme:

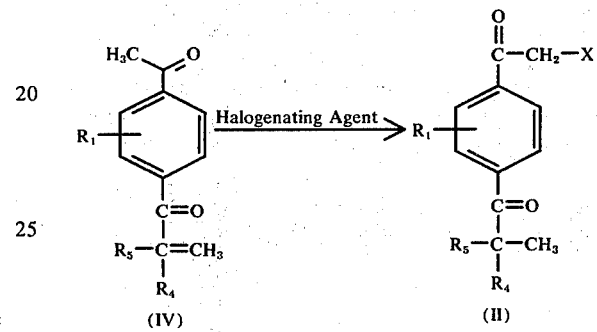

where
$R_1$, $R_4$, $R_5$ and X are as set out above.

The compounds of formula (II) are prepared by treating a compound of the formula (IV) with a halogenating agent in the presence of an inert organic solvent. The preferred halogenating agents for this particular reaction include chlorine or bromine, especially bromine. Although the particular solvent used is not critical, the preferred solvents are the halogenating hydrocarbons such as chloroform, carbon tetrachloride and the like, organic acids such as acetic acid or the ethers such as dioxane, tetrahydrofuran, or diethylether, the latter being especially preferred. The temperature of the reaction is not critical, but it is preferred that the reaction be carried out at a temperature between about −10° to 20° C, preferably from about 0° to 5° C. The reaction may be run from about 30 minutes to 2 hours, preferably from about 45 minutes to 75 minutes. The product is recovered as an oil using conventional techniques, e.g., evaporation or it may be used directly in the preparation of the compounds (I) as indicated above.

The compounds of formula (IV) may be prepared according to the following reaction scheme:

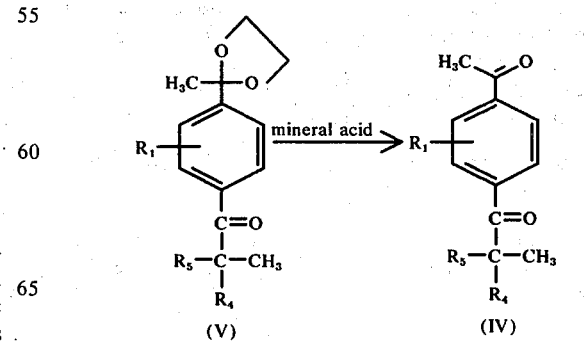

where

R₁, R₄ and R₅ are as set out above.

The compounds of formula (IV) are prepared by treating a compound of the formula (V) with an aqueous mineral acid. Where R₁ is hydrogen or halo, it is preferred that a concentrated mineral acid be used. When R₁ is lower alkoxy, it is preferred that a dilute mineral acid be employed. The acid can be hydrochloric acid, sulfuric acid, phosphoric acid, and the like. The particular acid used is not critical, but hydrochloric acid is preferred. Although a solvent is not required, an aqueous solvent could be employed such as water or a water soluble organic solvent e.g., the lower alkanols, or dioxane. The temperature of the reaction is not critical, but it is preferred that the reaction be carried out at about −60° to −180° C, especially the reflux temperature of the solvent. The reaction is run from about 12 to 48 hours, especially from about 16 to 20 hours. The product is recovered using conventional techniques, e.g., evaporation followed by distillation.

The compounds of formula (V) may be prepared according to the following reaction scheme:

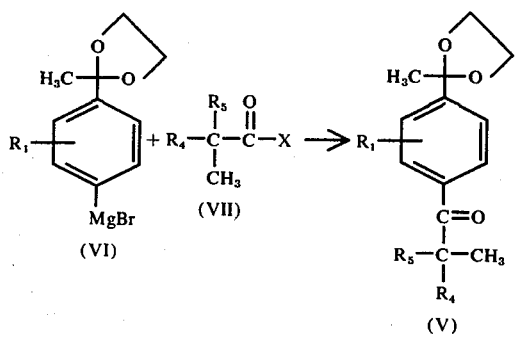

where

R₁, R₄, R₅ and X are as set out above.

The compounds of formula (V) are prepared by treating a Grignard reagent of the formula (VI) with an acid halide of the formula (VII) in the presence of an inert organic solvent. Although the particular solvent used is not critical, the preferred solvents are the ethers such as diethylether, dioxane or tetrahydrofuran, the latter being especially preferred. The temperature of the reaction is not critical, but it is preferred that the reaction be carried out from about 0° to −80° C more preferably from about −50° to −60° C. The reaction is run from about 1 to 5 hours, preferably from about 2 to 3 hours. The product is recovered using conventional techniques, e.g., evaporation.

The compounds of formula (VI), are prepared by well known procedures from compounds of the formula:

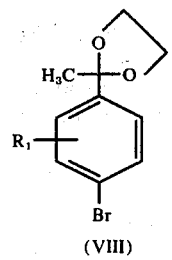

where

R₁ is as set out above.

Many of the compounds of formulae (VII) and (VIII) are known and may be prepared by methods described in the literature. The compounds of formulae (VII) and (VIII) not specifically disclosed may be prepared by analogous methods from known starting materials.

The compounds of formula (I) are useful because they possess pharmacological activity in animals, as hypolipidemic agents, particularly as hyperlipoproteinemic agents, as indicated by the fall in cholesterol and triglyceride levels in male albino Wistar rats weighing 110–130g. initially. The rats are maintained on drug-free laboratory chow diet for seven days and then divided into groups of 8 to 10 animals. Each group, with the exception of the control, is then given orally 30 milligrams per kilogram of body weight per diem of the compound for six days. At the end of this period, the animals are anesthetized with sodium hexobarbital and bled from the carotid arteries. Serum or plasma samples are collected, and 1.0 ml samples of the serum are added to 9.0 ml redistilled isopropanol. Two autoanalyzer cupsful of a mixture of zeolite-copper hydroxide and Lloydds reagent (Kessler, G., and Lederer, H., 1965, Technicon Symposium, Mediad Inc., New York (345–347) are added, and the mixture is shaken for one hour. Cholesterol and triglyceride levels are determined simultaneously on the same sample by Technicon N 24 A (chloresterol) and N-78 (triglyceride) methodology. The mean serum serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspension, dispersions, emulsions, and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base, and are readily prepared by reacting the base with an appropriate acid and, accordingly, are included within the scope of this invention. Representative of such salts are the mineral acid salts, such as the hydrochloride, hydrobromide, sulfate, phosphate and the like and the organic acid salts such as the succinate, benzoate, acetate, p-toluenesulfonate, benzene-sulfonate and the like.

The hypolipidemic effective dosage of compounds (I) employed in the alleviation of lipidemia may vary depending on the particular compound employed and the severity of the condition being treated. However, in general, satisfactory results are obtained when the compounds of formula (I) are orally administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 3000 milligrams. Dosage forms suitable for internal use comprise from about 75 to about 1500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg) |
| --- | --- |
| 4'-(4-methyl-1-piperazinylacetyl)pivalophenone | 100 |
| inert solid diluent (starch, lactose, kaolin). | 200 |

EXAMPLE 1

4'-(2-methyl-2-dioxolanyl) pivalophenone

To a suspension of 12.4 g (0.51 g-atoms) magnesium turnings in 190 ml tetrahydrofuran under a nitrogen atmosphere there is added 10 ml. of a solution of 103 g (0.424 mole) of 4'-bromoacetophenone ethylene ketal in 130 ml dry tetrahydrofuran. The reaction is started and the remainder of the bromoacetophenone ethylene ketal solution is added dropwise at a rate that maintains a moderate reflux. After the addition is complete, the mixture is refluxed for one hour. The resulting Grignard solution is added dropwise to a cold solution of 51.1 g (0.424 mole) pivaloyl chloride in 120 ml of dry tetrahydrofuran at a rate that maintains the temperature at 0° C. After addition the resulting solution is stirred for 1 hour at −60° C and then 1 additional hour at −10° C. The mixture is then poured onto ice and extracted with ether, the ether is washed with 2N sodium hydroxide and salt water, dried over anhydrous magnesium sulfate, filtered and evaporated in vacuo. The resulting residue is triturated with petroleum ether to give 4'-(2-methyl-2-dioxolanyl)pivalophenone, m.p. 75°–82° C.

Following the above procedure and using in place of 4'-bromoacetophenone ethylene ketal an equivalent amount of a. 4'-bromo-2'-chloroacetophenone ethylene ketal, or b. 4'-bromo-2'-methoxyacetophenone ethylene ketal, there is obtained a. 2'-chloro-4'-(2-methyl-2-dioxolanyl)pivolophenone, or b. 2'-methoxy-4'-(2-methyl-2-dioxolanyl)pivalophenone, respectively.

EXAMPLE 2

4'-acetylpivalophenone

A mixture of 70.3 g. (0.284 mole) 4'-(2-methyl-2-dioxolanyl) pivalophenone and 700 ml of 2N hydrochloric acid is refluxed for 18 hours. The resulting solution is cooled, extracted with ether, the ether washed with salt water, dried, evaporated and the resulting residue is distilled at 88°–86° C mm Hg to give 4'-acetylpivalophenone.

Following the above procedure and using in place of 4'-(2-methyl-2-dioxolanyl)pivalophenone an equivalent amount of a. 2'-chloro-4'-(2-methyl-2-dioxolanyl)pivalophenone, there is obtained a. 2'-chloro-4'-acetylpivalophenone.

Again following the above procedure and using in place of 4'-(2-methyl-2-dioxolanyl)pivalophenone an equivalent amount of (2-methoxy-2-dioxolanyl)-pivalophenone in the presence of a dilute hydrochloric acid in place of concentrated hydrochloric acid, there is obtained 2'-methoxy-4'acetylpivalophenone.

EXAMPLE 3

4'-(4-methyl-1-piperazinylacetyl)pivalophenone

To a solution of 27.2 g (0.134 mole) 4'-acetyl-pivalophenone in 200 ml of ether cooled to 0° there is added dropwise with stirring 21.5 g (0.134 mole) of bromine. The resulting pale yellow solution is washed with water and the ether is washed with brine, dried over anhydrous magnesium sulfate, filtered and evaporated to give an oil containing 38% unreacted 4'-acetyl-pivalophenone and 62% 4'-(bromoacetyl) pivalophenone. The resulting mixture is dissolved in 60 ml benzene and then added dropwise with stirring to a solution of 10 g (0.1 mole) N-methyl piperazine in 100 ml benzene while maintaining the temperature between 25° and 30° C. The mixture is then stirred for 18 hours at room temperature, the precipitate is filtered and washed with benzene, the excess benzene is washed with water and brine, dried over anhydrous magnesium sulfate, filtered and evaporated. The resulting residue is dissolved in ether and treated with hydrogen chloride gas, and the solid is recrystallized from methanol to give 4'-(4-methyl-1-piperazinylacetyl)pivalophenone m.p. 243°–246° C.

Following the above procedure and using in place of 4'-acetylpivolophenone an equivalent amount of a. 2'-chloro-4'-acetylpivalophenone or b. 2'-methoxy-4'-acetylpivalophenone, there is obtained a. 2'-chloro-4'-(4-methyl-1-piperazinylacetyl)-pivalophenone, or b. 2'-methoxy-4'-(4-methyl-1-piperazinylacetyl)-pivalophenone, respectively through the corresponding intermediates a. 2'-chloro-4'-(bromoacetyl)pivalophenone, or b. 2'-methoxy-4'-(bromoacetyl)pivalophenone respectively.

Again following the above procedure and using in place of N-methyl piperazine an equivalent amount of a. morpholine, or b. dimethylamine there is obtained a. 4'-(4-morpholinylacetyl)pivalophenone, b. 4'-(dimethylaminoacetyl)pivalophenone, respectively.

The 4'-(4-methyl-1-piperazinylacetyl)pivalophenone of this example is an effective hypolipidemic agent when orally administered to an animal suffering from lipidemia at a dosage of 150 mg. 4 times per day.

What is claimed is:

1. A compound of the formula

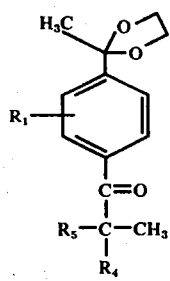

where
R₁ represents hydrogen, halo having an atomic weight of about 19 to 36, or straight chain lower alkoxy, and
R₄ and R₅ each independently represent alkyl having 1 to 2 carbon atoms.

* * * * *